US011083567B2

(12) United States Patent
Honigsbaum (10) Patent No.: US 11,083,567 B2
(45) Date of Patent: Aug. 10, 2021

(54) BIFURCATED HAPTIC ALIGNER-ACTUATORS FOR ACCOMMODATIVE INTRAOCULAR LENSES AND EXEMPLARY AIOLS ALIGNED AND ACTUATED THEREBY

(71) Applicant: Richard F. Honigsbaum, Passaic, NJ (US)

(72) Inventor: Richard F. Honigsbaum, Passaic, NJ (US)

( * ) Notice: Subject to any disclaimer, the term of this patent is extended or adjusted under 35 U.S.C. 154(b) by 498 days.

(21) Appl. No.: 15/839,152

(22) Filed: Dec. 12, 2017

(65) Prior Publication Data

US 2018/0161151 A1 Jun. 14, 2018

Related U.S. Application Data

(60) Provisional application No. 62/432,768, filed on Dec. 12, 2016, provisional application No. 62/448,740, filed on Jan. 20, 2017.

(51) Int. Cl.
*A61F 2/16* (2006.01)
*G02C 7/02* (2006.01)

(52) U.S. Cl.
CPC .......... *A61F 2/1624* (2013.01); *A61F 2/1613* (2013.01); *A61F 2/1629* (2013.01); *A61F 2/1635* (2013.01); *A61F 2/1648* (2013.01); *A61F 2/1662* (2013.01); *A61F 2002/169* (2015.04); *A61F 2002/1682* (2015.04); *A61F 2002/16901* (2015.04); *A61F 2250/0012* (2013.01); *G02C 7/02* (2013.01)

(58) Field of Classification Search
CPC .... A61F 2/1613; A61F 2/1629; A61F 2/1648; A61F 2002/1682; A61F 2002/169; A61F 2/1624; A61F 2/1635; A61F 2002/16091
See application file for complete search history.

(56) References Cited

U.S. PATENT DOCUMENTS

| | | | |
|---|---|---|---|
| 6,849,091 B1 | 2/2005 | Cumming | |
| 2004/0082994 A1* | 4/2004 | Woods | A61F 2/1613 623/6.34 |
| 2009/0018652 A1 | 1/2009 | Hermans et al. | |
| 2012/0078364 A1* | 3/2012 | Stenger | A61F 2/1629 623/6.39 |
| 2015/0035856 A1 | 2/2015 | Im et al. | |
| 2015/0035857 A1 | 2/2015 | Lowe et al. | |
| 2015/0035858 A1 | 2/2015 | Yang et al. | |
| 2015/0173892 A1 | 6/2015 | Borja et al. | |
| 2016/0361157 A1 | 12/2016 | Honigsbaum | |

FOREIGN PATENT DOCUMENTS

WO WO2014/134302 9/2014

* cited by examiner

*Primary Examiner* — William H Matthews
(74) *Attorney, Agent, or Firm* — Cozen O'Connor (57) ABSTRACT

Bifurcated haptic aligner actuators (BHAAs) have an anterior and a posterior lens support ring to each of which is pivotively attached a plurality of center-pivoted struts, at least two of which comprise an opposing pair, and to each of the opposing pair of struts is pivotably attached a bifurcated haptic, one haptic branch being pivotably attached to the anterior part of a strut, the other branch of the same haptic being similarly attached to the posterior part of the same strut.

10 Claims, 9 Drawing Sheets

BIFURCATED HAPTIC ALIGNER-ACTUATORS FOR ACCOMMODATIVE INTRAOCULAR LENSES AND EXEMPLARY AIOLS ALIGNED AND ACTUATED THEREBY

BACKGROUND OF THE INVENTION

1. Field of the Invention

The present invention relates to bifurcated haptic aligner-actuators for accommodative intraocular lenses (AIOLs). Specifically, the present invention relates to bifurcated aligner-actuators that both couple the actuating mechanisms of these lenses to the accommodating mechanisms of an eye and maintain alignment of the optical axes of these lenses with the optical axis of the eye.

2. Description of the Related Art

Some seventy years have elapsed since Sir Harold Ridley implanted a single-focus intraocular lens into the capsule of a human eye to restore distance vision lost to a cataractous crystalline lens and the extraction of that lens, and despite the obvious demand for an implant that is also accommodative, and the best efforts to date to provide same, no presently available accommodative intraocular lens (AIOL) approved by the United States Food and Drug Administration or otherwise provides a combination of the level of accommodation and the quality of vision provided by a properly fitted pair of progressive glasses.

AIOLs can, according to the prior art, be implanted into an eye from which the crystalline lens has been extracted, typically via anterior capsulorhexis, and either implanted directly into and actuated by the capsulorhexis-crippled capsule, or extra-capsularly and actuated directly by the ciliary body muscle.

An example of the former is published United States Patent Application 20090018652 to Hermans et al which discloses a two lens accommodative intraocular lens system for implantation into the capsule of an eye from which the crystalline lens has been extracted via capsulorhexis and, because it maintains separation between the anterior and posterior capsules and thus prevents shrink-wrapping, continues to function accommodatively as confirmed by the continuing functionality of Synchrony Vu™ AIOLs. Synchrony Vu™ AIOLs are not, however, approved for implantation by the USFDA.

Borja et al., published United States Patent Application 20150173892A1, is a further example of an actuator much like that disclosed by Hermans. Neither Boria nor Hermans, however, disclose or anticipate the bifurcated haptics of the present invention.

Prior art examples of ciliary muscle actuated AIOLs include Ichikawa et al, published United States Patent Applications 2015035856A1, 2015035857A1 and 2015035858A1, the first two of which are single lens configurations in which the lens is shown as being translated anteriorly by contraction of the ciliary body muscle, and the third is a two-lens configuration in which the anterior lens is intended to function as the single lens of the first two and the posterior lens is anchored into the capsulorhexis-compromised capsule. Once again there is no hint or suggestion of the bifurcated haptics of the present invention.

While direct attachment to or actuation by the ciliary body muscle arrangements such as those disclosed by Ichicawa would seem to be an obvious solution to problems such as capsule-implanted AIOLs being rendered inoperative by capsular shrinkwrapping and/or the loss by capsulorhexis of the centripetal capsular forces needed to effect accommodation of the AIOL, of the actuating mechanism of AIOL, such ciliary muscle arrangements have not proven to be well tolerated by the eye.

The present invention also includes configurations having anterior capsule tensioning rings, spacer-actuators and/or bellows-type hydraulic lenses, and these are mentioned (as are their initial disclosures) in published United States Patent Application PCT/US2014/019016 to Honigsbaum (the present inventor) and United States Patent Publication US20160361157A, also to Honigsbaum.

The present invention further includes bending grooves and pivots, and the former are described in Cumming, published U.S. Pat. No. 6,849,091 B1 and reduced to commercial practice in the Crystalens™ AIOL and the latter in the Hermans application and the Synchrony Vu™ AIOL respectively.

SUMMARY OF THE INVENTION

The bifurcated haptic aligner actuators (BHAAs) of this invention comprise an anterior and a posterior lens support ring to each of which is pivotively attached a plurality of center-pivoted struts, at least two of which comprise an opposing pair, and to each of the opposing pair of struts is pivotably attached a bifurcated haptic, one haptic branch being pivotably attached to the anterior part of a strut, the other branch of the same haptic being similarly attached to the posterior part of the same strut.

The haptics of this invention are intended for contact with and actuation by the accommodative mechanism of an eye, and their outboard ends are configured accordingly. Thus, because the AIOLs of this invention are further intended to be implanted in the capsule of an eye from which the crystalline lens has been extracted, and to be actuated with respect to accommodation and disaccommodation thereby, the outboard ends of the bifurcated haptics are configured to maintain contact with the inner perimeter of the capsule and to transfer changes in the capsule diameter to the AIOL foraactuation thereby.

While the AIOLs of this invention could, in theory, be implanted outside the capsule for direct actuation by the ciliary body muscle, such arrangements are not well tolerated by the eye, and their mention herein is not to suggest otherwise.

Because capsule-implanted AIOLs can be rendered inoperative with respect to accommodation by post-implantation shrink-wrapping of the capsule, the present invention also includes means such as a spacer-actuator to prevent same, and where appropriate, a tensioning ring to restore anterior capsule centripetal forces lost by capsulorhexis.

The actuators of this invention are intended to effect accommodation as response to a decrease in capsule diameter, that decrease being effected by a decrease in the centrifugal zonular tension, that tension being decreased by contraction of the ciliary body muscle, and the elasticity of the equatorial portions of the capsule surviving capsulorhexis.

Thus, if the AIOL comprises two fixed-focus lenses (one for each ring) and wherein the AIOL is made accommodative by increasing the spacing between the lenses, at least the struts pivotably connected to the bifurcated haptics would be tilted outward with respect to the lens rings (i.e., tangent to an ellipsoid), while if the AIOL comprises a hydraulic lens made accommodative by moving the rings closer together, these struts would be tilted inward (i.e., tangent to a hyperboloid).

Other objects and features of the present invention will become apparent from the following detailed description considered in conjunction with the accompanying drawings. It is to be understood, however, that the drawings and descriptions thereof are designed solely for purposes of illustration and explanation and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The following description, given with respect to the attached drawings, may be better understood with respect to the non-limiting examples of the drawings, wherein.

DETAILED DESCRIPTION OF THE PRESENTLY PREFERRED EMBODIMENTS

The description and the drawings herein to which the description refers are for purposes of explanation and illustration and are not for limiting the scope of the invention. The scope of the invention is defined by the claims.

Figure 1:
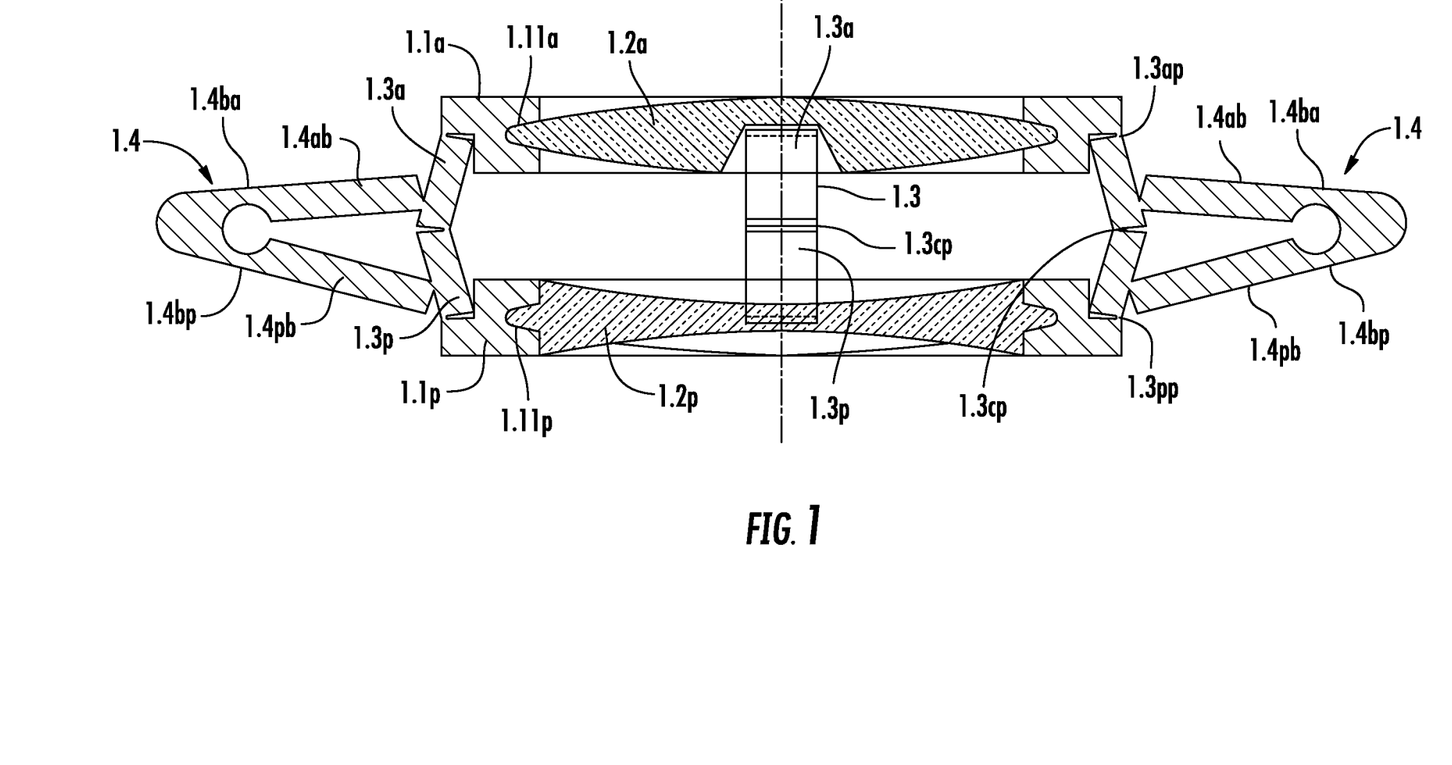
FIG. 1 is a sectional view of a bifurcated haptic aligner-actuator (BHAA) for a two-fixed-focus-lens AIOL in accordance with the present invention, and intended for implantation in, and actuation by, a lens capsule from which a crystalline lens, cataractous or otherwise, has been extracted via an anterior capsulorhexis.
Figure 3:
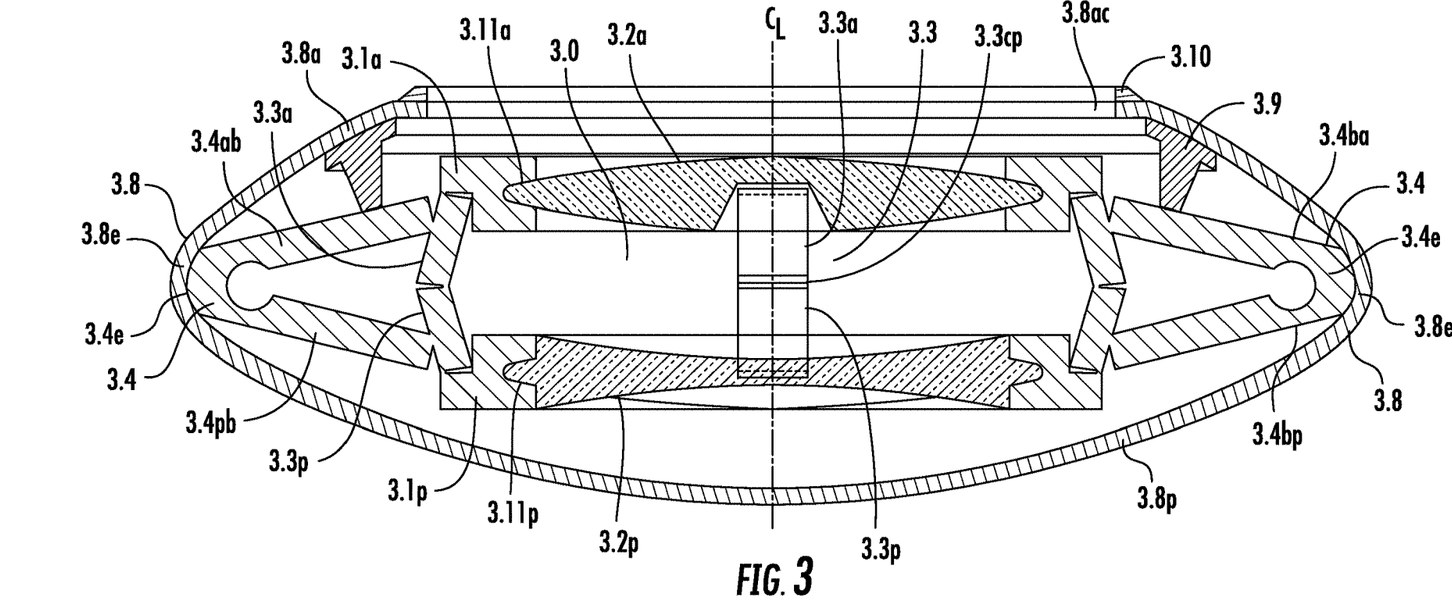
FIG. 3 is a sectional view of an AIOL in accordance with the present invention implanted in a capsule of an eye from which the crystalline lens has been extracted via anterior capsulorhexis.

FIG. 1 is a sectional view of a bifurcated haptic aligner-actuator (BHAA) actuated AIOL in accordance with the present invention, is generally identified by leader line 1.0 in the drawing, is intended for implantation in the capsule of an eye from which the crystalline lens has been extracted, and is shown so implanted in FIG. 3.

The BHAA portion of AIOL 1.0, which is the focus of the present invention, comprises a pair of lens rings, anterior lens ring 1.1a and posterior lens ring 1.1p, and each lens ring further comprises a lens retention means, here shown as grooves 1.11a and 1.11p respectively, and into each groove is affixed, fixedly or otherwise, the appropriate one of a biconvex anterior AIOL lens 1.2a and biconcave posterior AIOL lens 1.2p. The rings can, of course, alternatively be ridged and the lenses grooved to retain the latter, but the arrangement shown is in the drawing is presently preferred. Further, the rings can be an integral part of the lenses and vice versa.

Anterior lens 1.2a is shown and described as biconvex because it also corrects for the loss of the crystalline lens and posterior lens 1.2p as biconcave because the biconvex-biconcave combination is preferred for two lens AIOLs, but at least one the refractive surfaces of these lenses can be configured otherwise where appropriate. Examples of such other configurations include, but are not limited to: cylindrical or toric to correct for astigmatism, aspheric to correct for distortions introduced by hydraulic and/or thick (high diopter) spherical surface lenses, prismatic to facilitate convergence, etc. If prismatic, such correction would, of course, be applied to posterior lens 1.2p to avoid intentional misalignment of the optical axis of lens 1.2a with respect to the optical center of lens 1.2p.

If these corrections were applied to lenses 1.2a, 1.2p, etc., they would, excepting those correcting only for extraction of the crystalline lens, strictly speaking, be net positive and net negative respectively, but are shown and described as biconvex and biconcave respectively herein for convenience of description and illustration. The terms "net positive" and "net negative" refer to lenses that are suitable for use in embodiments of the present invention, and are defined as such later herein.

Lens rings 1.1a and 1.1p are coupled to one another by a plurality of at least three triply pivoted struts 1.3, a sub-plurality "n" of which are spaced 360/n degrees apart, and wherein "n" for FIG. 1 is two and the two are spaced 180 degrees apart. Each strut further comprises an anterior part 1.3a pivotably connected to anterior ring 1.1a at its anterior end by anterior strut to anterior lens ring pivot 1.3ap, a posterior part 1.3p pivotably connected to posterior ring 1.1p by posterior strut pivot 1.3pp and a center pivot 1.3cp pivotably connecting each anterior strut part 1.3a to posterior part 1.3p of the same strut 1.3.

Each of the "n" struts is pivoted in such a way that center pivot 1.3 moves outward (away from the centerline shown in the drawing) when lens rings 1.1a and 1.1p are brought closer together, and the actuator portion of AIOL 1.0 further comprises a bifurcated haptic 1.4 for each "n" strut, each bifurcated haptic having an anterior branch 1.4ab pivotably connected to the anterior part 1.3a of the corresponding "n" strut and a posterior branch 1.4pb pivotably connected to the posterior part 1.3p of the same strut.

Thus, when capsule 3.8 of FIG. 3 contracts, haptics 1.4 move centripetally as do center strut pivots 1.3c, rings 1.1a and 1.1p, lenses 1.2a and 1.2p move farther apart, and the AIOL becomes accommodative, and vice versa.

The bifurcated haptic actuator portion of AIOL 1.0 also optionally includes provisioning for biasing the AIOL accommodatively or disaccommodatively as appropriate, and the choice is explained in greater detail in the descriptive material for FIG. 3 herein.

This biasing can be provided by bending groove type pivots as illustrated and described in further detail with respect to FIGS. 7a through 7d, by reduced cross section haptic branch biasing portions 1.4ba, 1.4bp as presently preferred, by springs (not shown) connecting the branches of a haptic, or by a combination of these.

While persons of ordinary skill in the art will recognize that AIOLs like those of FIG. 1 would still be accommodative if posterior lens 1.2p were omitted, their accommodative range would be inferior to those of FIG. 1, and are not, for this reason a presently preferred embodiment.

Figure 2:
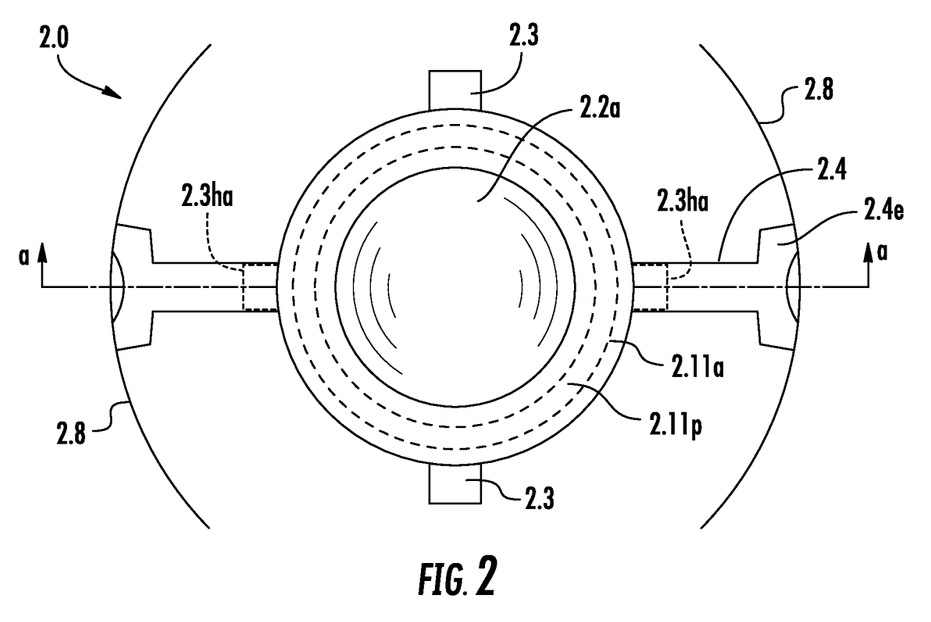
FIG. 2 is an anterior plan view of the AIOL of FIG. 1.

FIG. 2, here identified by leader line 2.0 is an anterior plan view of bifurcated haptics AIOL 1.0 of FIG. 1 in lens capsule 2.8, and visible and shown in the drawing are anterior lens 2.2a, struts 2.3, bifurcated haptics 2.4, bifurcated haptic outboard ends 2.4e, and cutting plane line aa which defines the cutting plane for FIG. 1, and by analogy, for other drawings herein where appropriate, as well. Also shown, but not visible in a plan view and shown dotted are anterior and posterior lens grooves 2.11a, 2.11p, and haptic-adjacent struts 2.3ha.

Two haptic AIOLs are notorious for tilting the lens assembly as its focus changes from accommodating to disaccommodating and vice versa, and while this can be addressed here by introducing a greater plurality of haptics, e.g. "n>2", where each bifurcated haptic is affixed to one of the plurality of "n>2" 1.3 FIG. 1 struts spaced 360/n degrees apart, a plurality of haptics greater than two seriously complicates implantation, and tilt is seldom so addressed even for non-accommodating IOLs for this reason.

Tilt in the present invention is instead addressed by struts, 1.3 in FIGS. 1 and 2.3 in FIG. 2, and by the configuration of the parts of the outboard ends of the haptics in contact with lens capsule 2.8 (lens capsule 3.8 of FIG. 3).

With respect to the struts, for example, differences in the biasing forces between the left and the right hand haptics of FIG. 1 that try to change the spacing between the left-most edges of rings 1.1a, 1.1p with respect to the right-most edges of those rings would apply a torque to the struts and pivots in the center of FIG. 1 (the upper and lower struts 2.3 in FIG. 2) and be resisted thereby. Analogously, if forces tried to change the spacing between the upper and lower edges at the center of rings 1.1a, 1.1p in FIG. 1 (the edges connected to the upper, and lower struts in FIG. 2) these forces would apply a torque not only to the left and right struts, but also to the haptics which are pivotably connected thereto, and be resisted thereby.

Figure 2A:
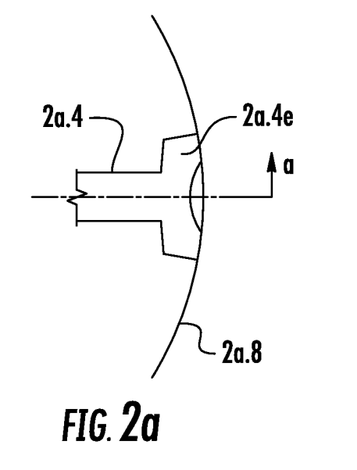
FIG. 2a is a fragmentary sectional plan view of an outboard end of a bifurcated haptic appropriate for a capsule-actuated AIOL and in accordance with the present invention.
Figure 2B:
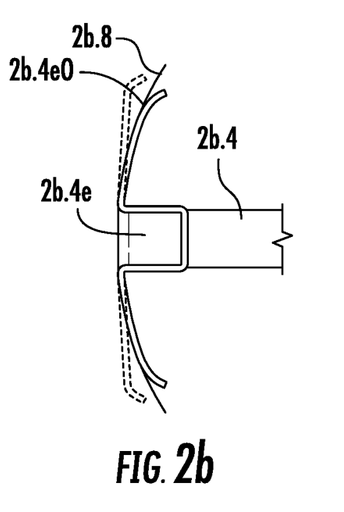
FIG. 2b is a fragmentary sectional plan view of an alternative configuration of an outboard end configuration of FIG. 2a and in accordance with the present invention.

With respect to forces that would otherwise tilt the optical axis of the AIOLs of this invention with respect to that of the eye, the parts of the outboard ends of the haptics (1.4e in FIGS. 1 and 2.4e, 2a.4e and 2b.4e in FIGS. 2, 2a and 2b respectively) in contact with capsule 2.8 are contoured as shown in FIGS. 2, 2a and 2b, thus resulting in spaced-apart haptic-capsule equator contact areas which would distort the local equatorial region of capsule 2.8 (3.8 of FIG. 3) and thus provide a torque that, resists tilt about an axis parallel to cutting plane line aa of FIG. 2.

While haptic ends 2.4e and 2a.4e of FIGS. 2 and 2a are shown as rigid, those of FIG. 2b are flexible as are those of conventional IOLs, and the pre-implantation configurations of the flexible parts (the outriggers) are shown as dotted lines, and their post implantation configurations as solid lines. Depending upon the stiffness of outriggers 2.4beo, the restorative forces with respect to lens axis tilt are provided by distortion of capsule 2b.8, outriggers 2b.4eo, or both.

FIG. 3 is a sectional view, the cutting plane for which is analogous to cutting plane aa of FIG. 2, but is defined by the centerline shown in FIG. 3. The AIOL identified by leader line 3.0 in the drawing is shown having a bifurcated aligner-actuator in accordance with the present invention, but is implanted in lens capsule 3.8 from which the crystalline lens has been extracted and is actuated with respect to accommodation-disaccommodation by the change in capsule diameter as noted with respect to FIG. 1.

Now familiar from FIGS. 1 and 2 and analogously so identified are anterior and posterior lens rings 3.1a and 3.1p, anterior and posterior lens grooves 3.11a and 3.11p, and anterior and posterior lenses 3.2a and 3.2p respectively. FIG. 3 shows lenses 3.3a and 3.3p as biconvex and biconcave respectively as in FIG. 1, and the alternatives mentioned with respect to FIG. 1 are also applicable here.

Also familiar are the plurality of at least three center-pivoted struts 3.3 at least two of which are spaced 180 degrees apart, the pivotal coupling of the anterior parts 3.3a of struts 3.3 to anterior ring 3.1a and the posterior parts 3.3p to posterior ring 3.1p and the pair of bifurcated haptics 3.4, the anterior and posterior branches 3.4ab 3.4pb of which are pivotably coupled to the anterior parts 3.3a and 3.3p of a pair of 180 spaced struts, all of which are as shown in the drawing.

The haptic ends presently preferred for the capsule-implanted AIOLs of this invention are those of FIGS. 2, 2b and 2c, and they have been described in detail with respect to those drawings earlier herein.

Haptics 3.4 of FIG. 3 serve the same general purposes as haptics 1.4 of FIG. 1 in that they fix AIOL 3.0 in place in the eye, couple it to the accommodative mechanism of the eye and prevent tilt with respect to an axis parallel to cutting plane line aa of FIG. 2, except that they are held in place in capsule 3.8 by the centripetal forces provided by anterior capsule 3.8a and the centrifugal forces provided by spacer-actuator 3.9 as explained in greater detail below, and the tilt mentioned immediately above is resisted by haptic ends 2a.4e, 2b.4e, as explained with respect to FIGS. 2, 2a and 2b herein.

Capsule 3.8 has an anterior part 3.8a and a posterior part 3.8p, and while the posterior part is maintained in the approximate shape shown by its zonules (not shown) which insert at the anterior hyaloid membrane (again not shown) before inserting at posterior capsule 3.8p, the contour of the anterior capsule is maintained by the crystalline lens which, once extracted, allows the anterior capsule to fuse to the posterior capsule, shrink-wrapping haptics 3.4 and rendering the AIOL inoperative with respect to accommodation in the absence of something to prevent this.

Documentation for the consequences of shrink-wrapping includes:

Study of the force dynamics at the capsular interface related to ciliary body stimulation in a primate model, Alio, J L et al, J. Refract Surg 2015 Febuary 31(2) 124-8 2015, and validation for this with respect to Crystalens™ includes:

Aberrometry in patients implanted with Accommodative Intraocular Lenses, Perez-Marino, P. et al, Am J. Ophthalmol. 2014 Feb. 13.

The FIG. 3 embodiment therefore includes spacer-actuator 3.9 which is in contact with both anterior capsule 3.8a and haptics 3.4, and not only prevents the above-mentioned shrink-wrapping, but also transmits disaccommodative forces from anterior capsule 3.8a to haptics 3.4 and thus to AIOL 3.0, all of which is explained in greater detail in published document WO2014/134302 to Honigsbaum mentioned previously herein.

Anterior capsule 3.8a also includes capsulorhexis 3.8ac, which is the surgically created opening via which the crystalline lens is extracted and AIOL 3.0 and spacer-actuator 3.9 are implanted, and this surgery also removes not only some of the anterior capsule elastic fibers but also the disaccommodative forces produced thereby.

Thus FIG. 3 embodiments also optionally include tensioning ring 3.10, which restore centripetal anterior capsule forces lost by capsulorhexis and the above-mentioned disaccommodative forces lost thereby, again as explained in PCT/US2014/019016.

Figure 7A:
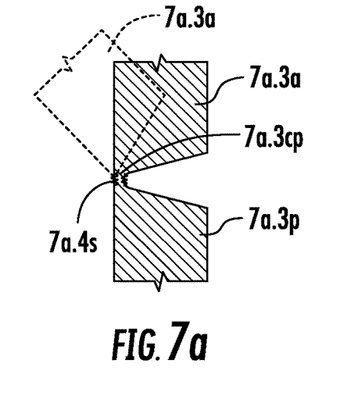
FIGS. 7a through 7g are detail drawings of strut, strut-to-lens-ring and strut-to-haptic pivots in accordance with the present invention.
Figure 7B:
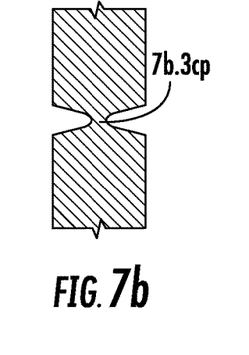
Figure 7C:
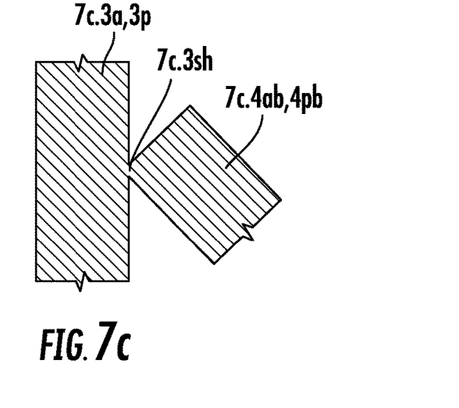

Biasing for FIG. 3 embodiments is provided as for the embodiments of the AIOLs of FIG. 1, i.e., by bending groove type pivots as illustrated and described in further detail with respect to FIGS. 7a through 7c, by reduced cross section haptic branch biasing portions 3.3ba, 3.4bp, by a spring (not shown) connecting the branches of a haptic, or by a combination of these. Biasing for the AIOLs of FIG. 3 embodiments is again, accommodative as for the FIG. 1 embodiments implanted herein, disaccommodative biasing for FIG. 3 embodiments being provided by spacer-actuator 3.9 and anterior capsule 3.8a. as in the Honigsbaum reference mentioned previously herein.

Because posterior rings 3.1p of FIG. 3 can contact posterior capsule 3.8p and serve as a conduit for the migration and growth of cells that cause posterior capsular obscuration (PCO), at least the outer posterior edge of the posterior rings of FIG. 3 embodiments are preferably sharp enough to discourage this.

Figure 6:
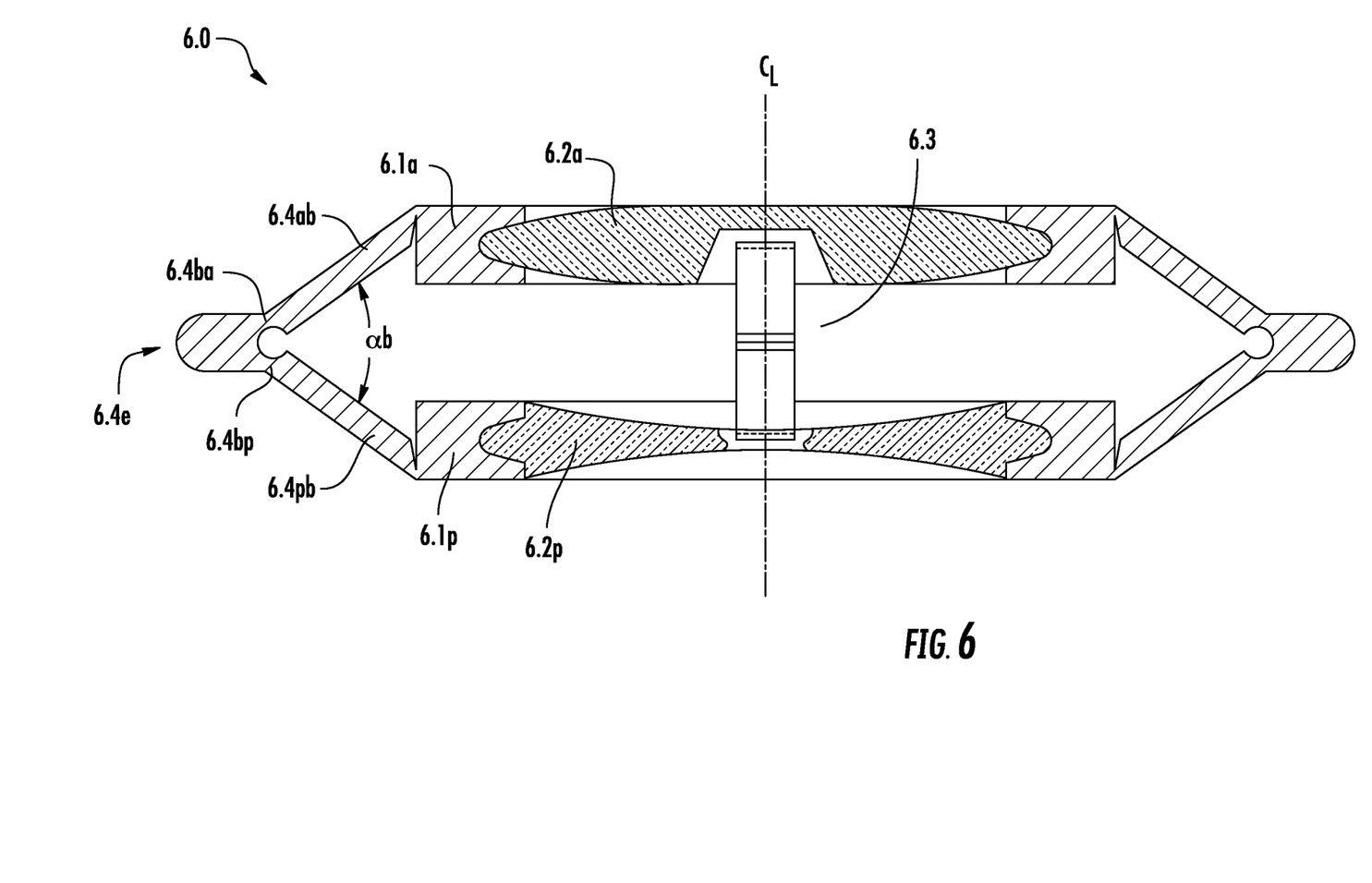
FIG. 6 is a simplified version of the BHAA of FIG. 1, and in accordance with the present invention.

FIG. 4 is again a sectional view of a bifurcated haptic AIOL, here identified by leader line 4.0, the cutting plane for which is analogous to cutting plane aa of FIG. 2 but is defined by the centerline shown in FIG. 4, and both it and its embodiments are AIOLs having bifurcated haptic aligner-actuators in accordance with the present invention as do those of FIGS. 1, 3 and 6.

Figure 4:
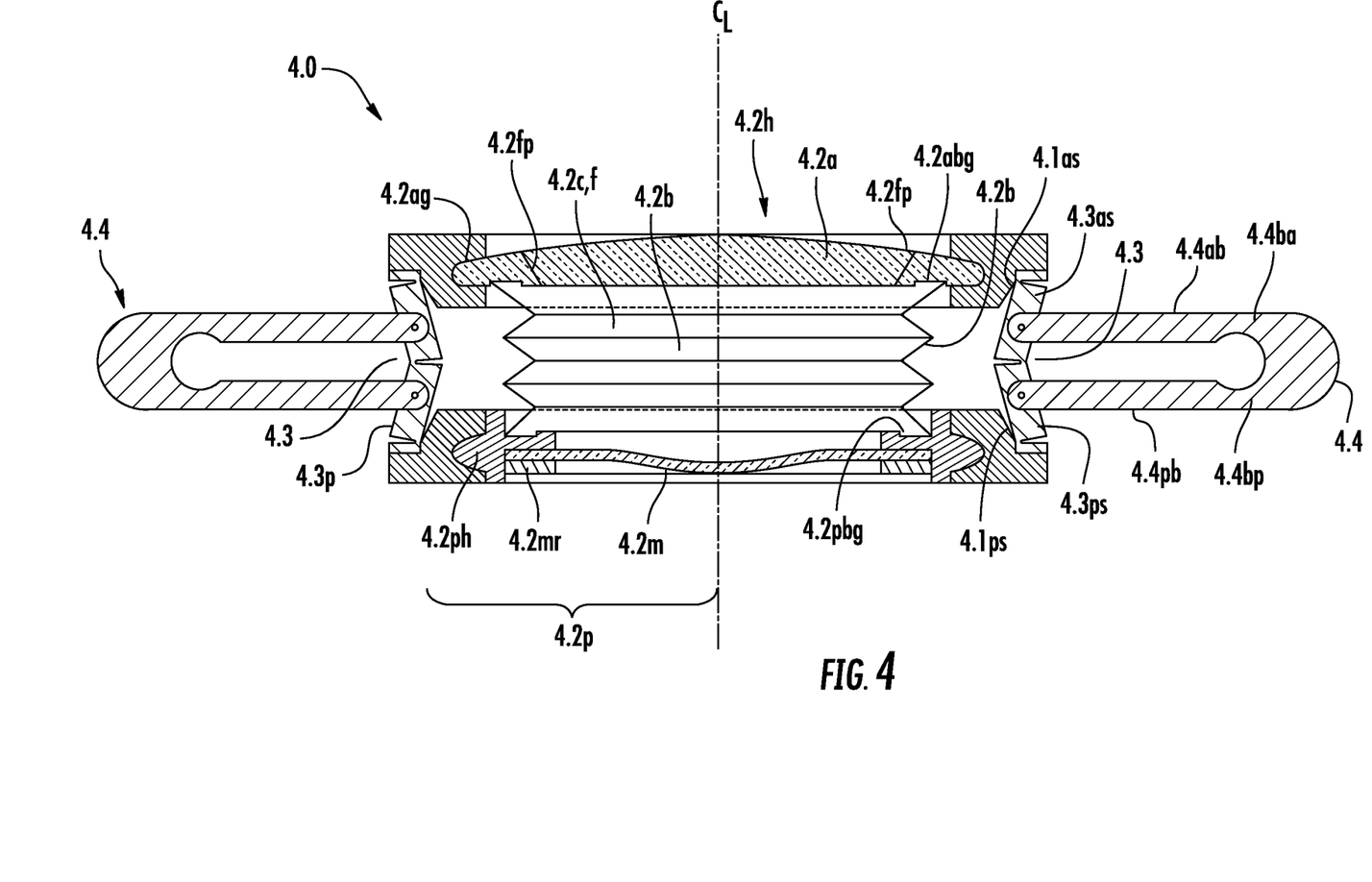
FIG. 4 is a sectional view of a hydraulic AIOL in accordance with the present invention implanted in the capsule of an eye from which the crystalline lens has been extracted.

FIG. 4 and its embodiments, however, include bifurcated haptic aligner-actuator-actuated adjustable-focus hydraulic lenses 4.2h in lieu of the pair of fixed-focus lenses of FIGS. 1, 3 and 6.

The hydraulic lenses 4.2h of FIG. 4 and its embodiments comprise a plano-convex fixed focus lens 4.2a, a membrane assembly 4.2p comprising a membrane holder 4.2ph, a membrane ring 4.2mr and a transparent elastically reconfigurable membrane 4.2m fixedly sandwiched between the posterior face of membrane holder 4.2ph and membrane ring 4.2mr, a bellows 4.2b the anterior end of which is fixedly affixed to the posterior face of plano-convex lens 4.2a and preferably to an optional bellows groove 4.2ag therein and the posterior end of which is fixedly affixed to the anterior face of membrane holder 4.2p which also preferably further comprises a bellows groove, and if so, to bellows groove 4.2phg.

The hydraulic lens portion 4.2h of FIG. 4 also includes a refractive hydraulic fluid 4.2f having an index of refraction greater than that of aqueous humor and confined within a hydraulic chamber 4.2c defined by anterior lens 4.2a, posterior membrane assembly 4.2ph, bellows 4.2b, and optional fill-purge ports 4.2fp.

The bifurcated haptic AIOL of FIG. 4 is made accommodative by moving bifurcated haptics 4.4 centripetally, which also moves the center pivots of pivoted struts 4.4 centripetally and lens rings 4.1a, 4.1p closer together, thus moving hydraulic fluid from the portion of hydraulic lens assembly 4.2h defined by bellows 4.2b to that defined by membrane assembly 4.2p, increasing the anterior curvature of membrane 4.2m, and of course, that of the refractive posterior face of the hydraulic fluid 4.2f adjacent thereto.

Because this FIG. 4 accommodation is effected in just the opposite way from that of the FIGS. 1, 3 and 6 embodiments but must still be effected by the accommodative mechanism(s) of an eye, struts 4.3 are pivoted in just the opposite direction from struts 1.3 and 3.3 of FIGS. 1 and 3 respectively, and are thus tangent to a hyperboloid rather than to a ellipsoid as in the previously mentioned drawings and their embodiments. Because this pivoting could conceivably allow struts 4.3 to contact and damage bellows 4.2 under extreme attempts at accommodation, the strut 4.3—adjacent faces 4.1as, 4.3.as and 4.1ps, 4.3ps of lens rings 4.1a, 4.1p respectively are preferably configured as shown, and if so, will prevent this.

The struts 4.3 of FIG. 4 are, it should be noted, configured somewhat differently from those of FIGS. 1, 3 etc., each strut of FIG. 4 having not only a center pivot 4.3pc, but also pivotably connected end portions 4.3e fixedly affixed to lens rings 4.1a,p respectively. Struts 1.3 and 3.3 of FIGS. 1 and 3 respectively can, of course, be alternately so configured as well.

FIG. 4 and its embodiments also include a pair of 180 degree spaced bifurcated haptics 4.4 (only two bifurcated haptics for reasons explained earlier herein) each of which is shown as having now familiar anterior and posterior branches 4.4a, 4.4b, anterior and posterior branch biasing portions 4.4ab, 4.4pb; and each anterior branch is pivotably connected to an anterior portion 4.3a of one of a pair of 180 degree spaced struts 4.3 and each posterior branch is pivotably connected to a posterior portion 4.3p of the same pair of 180 degree spaced struts.

The outboard ends 4.4e of haptics 4.4 of FIG. 4 are configured for coupling to the accommodative mechanism of an eye, and are here intended for coupling to a capsule as in FIGS. 1 and 3, and have outboard ends as illustrated and described with respect to FIGS. 2, 2a and 2b.

While hydraulic lens assembly 4.2h is shown affixed, fixedly or removeably, to AIOL 4.0 by fixed focus lens 4.2a inserted into lens groove 4.11a and membrane holder 4.2ph inserted into lens groove 4.11p, persons of ordinary skill in the art will recognize that an equally effective configuration, but one less convenient for purposes of manufacture could comprise an anterior lens configured to also serve as anterior ring 4.1a and a posterior ring configured to serve as both membrane holder 4.2ph and posterior ring 4.1p.

FIGS. 5a-5d are link and pin (strut, haptic and pivot) representations of the various configurations of the bifurcated haptic aligner actuators of this invention, and in which straight solid lines represent lens rings, struts and haptics, solid black circles represent pins (pivots) and solid black circles within open circles represent pins (pivots) that couple bifurcated haptic branches to struts that are not pivoted at the point of coupling. Bifurcated haptic actuators of disaccommodated AIOLs are represented by solid lines and those of accommodated AIOLs by dashed lines, so that, with reference to FIG. 5a, the upper (solid line) in the drawing is a link and pin representation of a disaccommodated version of FIGS. 1 and 3, and the lower (dashed line) drawing is a link and pin representation of an accommodated version of the same AIOLs.

Figure 5A:
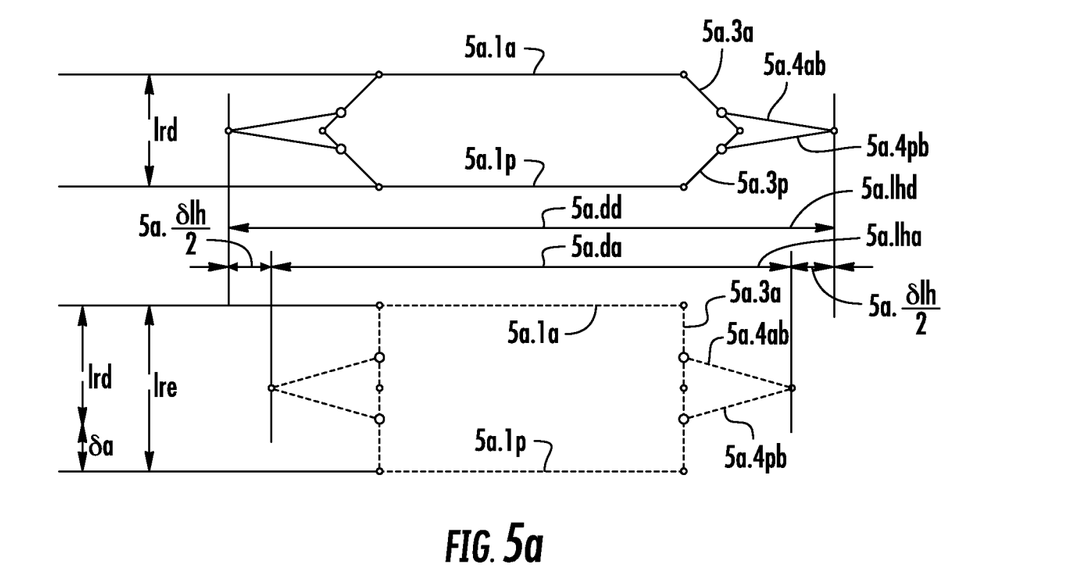
FIGS. 5a through 5d are link-and-pin representations of the BHAAs of the present invention.

Thus, as is clear from FIG. 5a, the change in the distance between the outboard ends of haptics δ lh, (twice the dimension δlh/2 shown in the drawing) resulting from accommodative contraction of the lens capsule results in the change in lens ring 5a.1a-5a.1b spacing and thus the accommodative change in anterior-posterior lens spacing δa.

Figure 5B:
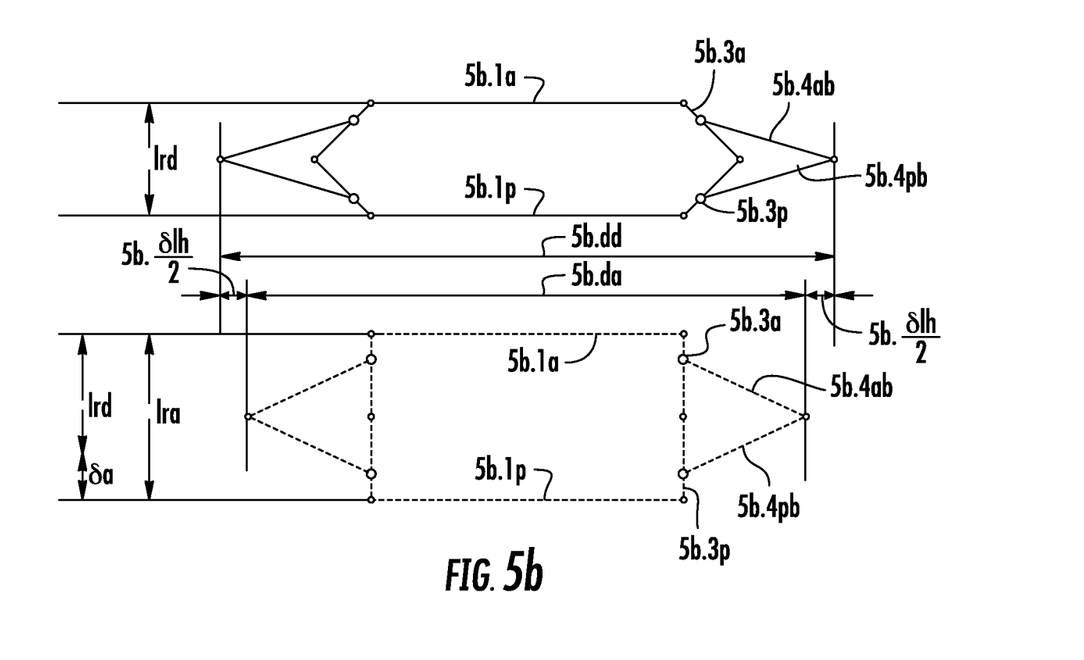

FIG. 5b is a drawing much like that of FIG. 5a excepting the positioning of the haptic branches 5b.4ab, 5b.4pb with respect to anterior and posterior strut portions 5b.3a, 5b.3b, which is closer to rings 5b.1a, 5b.1p as shown, and the result, as is clear from the drawing, is that an accommodative change δa in the spacing between lens rings 5b.1a, 5b.1p corresponding to that of FIG. 5a is effected by a smaller change in the aforementioned capsule diameter δlh.

Figure 5C:
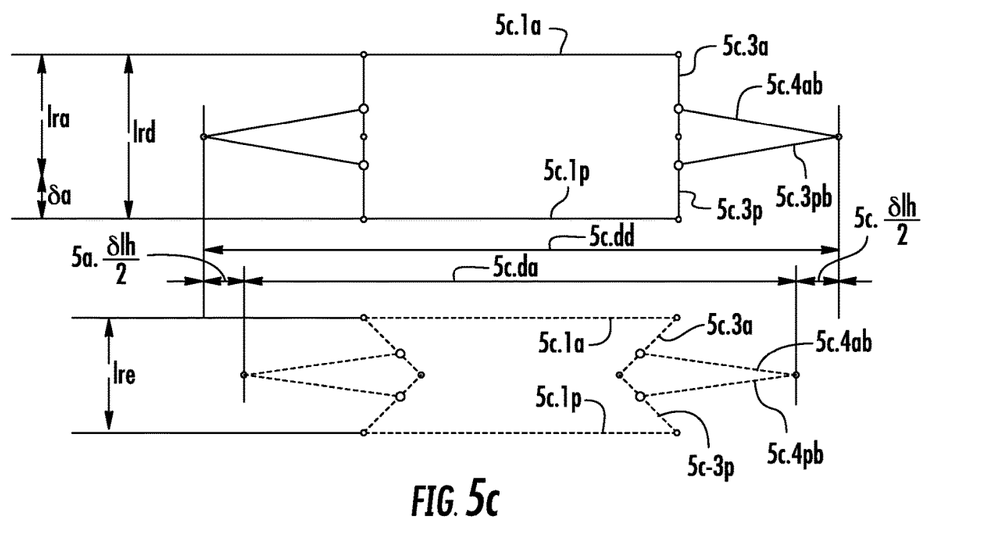

FIG. 5c is a link and pin representation of a bifurcated haptic aligner-actuator of the present invention for use with a hydraulic lens such as that of FIG. 4, but because such hydraulic lenses are made accommodative by moving the lenses corresponding to 5c.1a, 5c.1b closer together, the struts and haptics are configured accordingly, as shown. Thus again the same change in capsule diameter, (dd−da)=2(δlh/2) results in the same change in ring spacing δa as in FIG. 5a, but in the opposite direction.

FIG. 5d is once again a link and pin representation of a bifurcated haptic aligner-actuator of the present invention, and is much like FIG. 5b except that here only the bifurcated haptic branches 5d.4pb are moved closer to lens ring 5d.1p, and the result is not only the same change in lens ring spacing for the same change in capsule diameter, but also a change in the anterior-posterior positioning of lens rings 5d.1a, 5d.1p (and thus the lens portion of the AIOL) with respect to haptic outboard ends 5d.4he.

Figure 5D:
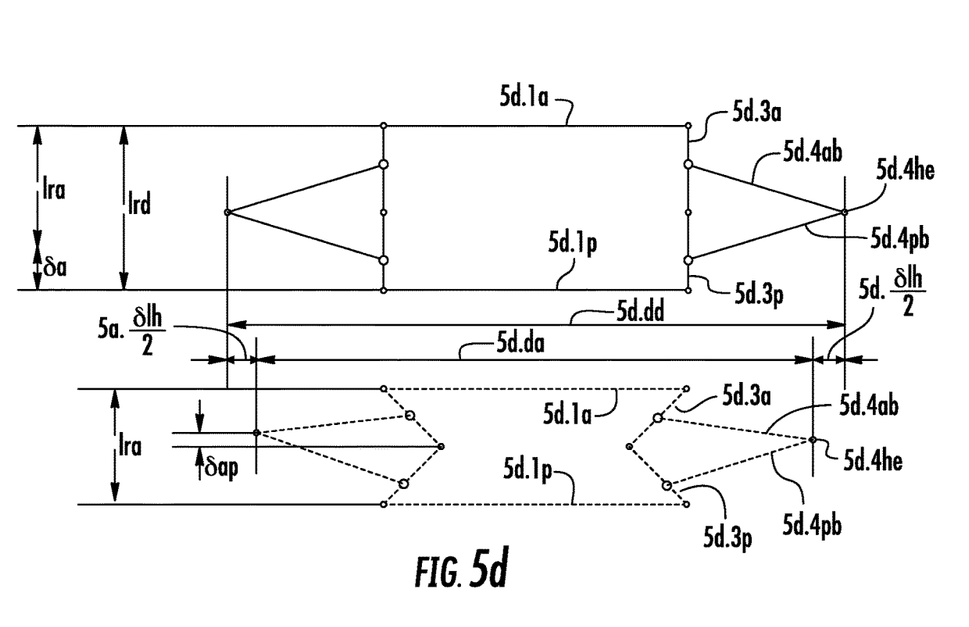

The advantages of embodiments in accordance with FIG. 5d include FIG. 3 embodiments that provide a greater range of accommodation without the risk that parts of the anterior capsule that survive capsulorhexis will make contact with the iris and compromise aqH drainage, FIG. 6 is again a sectional view of a bifurcated haptic AIOL, here identified by leader line 6.0, the cutting plane for which is analogous to cutting plane aa of FIG. 2 but is defined by the centerline shown in FIG. 6, and both it and its embodiments are AIOLs having bifurcated haptic aligner-actuators in accordance with the present invention.

FIG. 6 and its embodiments are much like those of FIG. 1, and familiar therefrom and shown in FIG. 6 are anterior and posterior lens rings 6.1a, 6.1p and lenses 6.2a, 6.2p, bifurcated haptic anterior and posterior branches 6.4ab, 6.4pb having anterior and posterior biasing portions 6.4ba, 6.4bp respectively, bifurcated haptic outboard ends 6.4e configured for actuation with respect to accommodation and disaccommodation by a lens capsule as per FIGS. 2, 2a and 2b, and center-pivoted struts 6.1.

Bifurcated haptic branches 6.4ab, 6.4pb are not, however, pivotably coupled to anterior and posterior portions of center-pivoted struts as in FIG. 1, but are instead pivotably connected to anterior and posterior rings 6.1a, 6.1p as shown, the bifurcated FIG. 6 branches 6.ab, 6.pb, biasing portions 6.4ba 6.4bp and haptic end portions 6.4e also serving as strut-haptics, i.e., both as haptics and as center-pivoted struts.

Successful actuation of FIG. 6 embodiments with respect to accommodation and disaccommodation, however, requires an angle "α" between the bifurcated haptic branches 6.4ab, 6.4pb large enough to effect separation of the rings and thus accommodation as response to contraction of the capsule into which it is implanted, and while an angle "α" of 60 degrees as shown in FIG. 6 or an even greater angle is certainly large enough to do so, an angle of approximately zero degrees as in FIG. 4 certainly will not, and the 30 degree angle of FIG. 1 is doubtful.

Figure 7D:
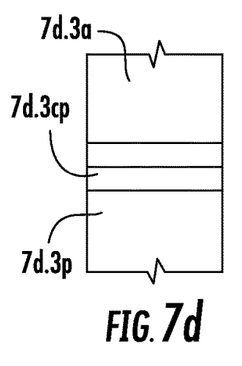
Figure 7E:
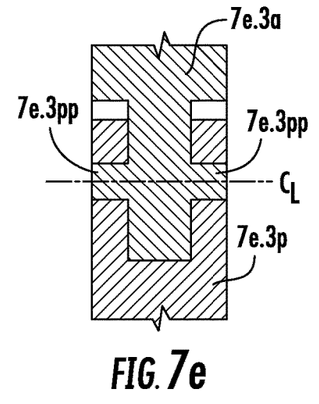
Figure 7F:
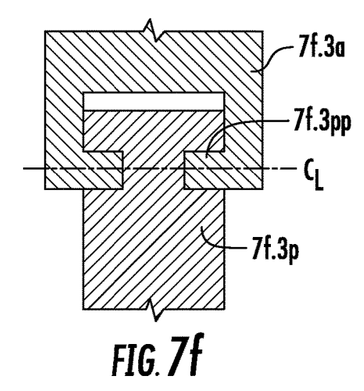
Figure 7G:
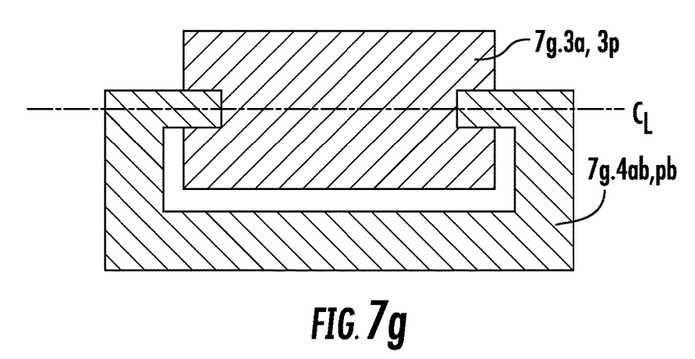

FIGS. 7a through 7g are pivot configurations for the embodiments of FIGS. 1-6 and 8: those of FIGS. 7a through 7d being bending groove configurations and those of FIGS. 7e through g more conventional hinges.

Pivoting of FIG. 7a and its embodiments is effected by rotating, e.g., the anterior part of strut 7a.3a about center pivot (bending groove) 7a.3cp with respect to posterior part 7a.3p to the dotted position shown in the drawing. (Materials that are biocompatible, that can survive repeated bending of the kind mentioned and that are suitable for the applications intended herein are known from the prior art as mentioned earlier herein.)

FIG. 7b is an alternative bending groove type pivot in which bending portion 7b.3cp is centrally positioned instead of on one side as in FIG. 7a, and serves as an introduction to FIG. 7c, in which bending portion 7c.3sh serves as a bending groove type pivot connecting anterior and posterior haptic branches 7c.4ab, 4bp to strut segments 7c.3a, 3p respectively, as shown and identified by leader lines 1.3sh in FIG. 1.

FIG. 7d is a view of the strut portion of FIG. 7a looking from the right, FIG. 7b from the right or left, and FIG. 7c from above or below, and its purpose will become clear after the description of FIGS. 7e through 7g.

FIG. 7e is a sectional view of a hinge-type pivot familiar from the prior art, the hinge pin equivalent 7e.3pp of which is an integral part of anterior strut 7e.3a, is therefore captive with respect to the BHAA, and which can serve as the pivotal connection 1.3cp between anterior and posterior struts 1.3a, 1.3p, between struts 1.3 and rings 1.1a, 1.1p of FIG. 1, its embodiments, and the analogous parts of other drawings herein and their embodiments as well.

FIG. 7f is a pivotal connection alternative to that of FIG. 7e, and in both the hinge pin equivalents 7e.3pp, 7f.3pp are integral with anterior strut segments 7e.3a, 7f.3a but can, of course, alternately be integral with posterior strut segments 7f.3p, 7f.3p instead. A further alternative is a non-integral pin arrangement such as is familiar from door hinges, cabinet hinges, etc., but such arrangements introduce the further problems of pin retention and the consequences of its loss and damage to the eye.

Comparing FIG. 7d with FIGS. 7e and 7f it is clear that the whole width of bending groove 7d.3p is available to serve the tilt resisting mechanism described with reference to FIG. 2 but not in FIGS. 7e and 7f, and that the tilt-resisting mechanism is further compromised by the clearances between 7e.3pp and 7f.3pp needed to accommodate pivoting.

FIG. 7g is a hinge-type alternative to a FIG. 7c arrangement for coupling bifurcated haptic branches 7g.4ap, 4pb to anterior and posterior parts of struts 7g.3a, 3p, and is of particular interest with respect to FIG. 4 embodiments, where at least the bifurcated haptic-coupled struts are tangent to a hyperboloid, and where bending grooves such as those of FIG. 7c could allow contact between non-pivot parts of the bifurcated haptics and the struts during accommodation and reduce the accommodative range of FIG. 4 embodiments thereby.

FIG. 8 is again a sectional view of a bifurcated haptic AIOL, here identified by leader line 8.0, the cutting plane for which is analogous to cutting plane aa of FIG. 2 but is here defined by the centerline shown in FIG. 8, and both it and its embodiments are AIOLs having bifurcated haptic aligner-actuators in accordance with the present invention, and their embodiments are versions of FIG. 6 that have been modified to actuate hydraulic lenses such as those of FIG. 4, and immediately recognizable therefrom are anterior ring 8.1a having lens groove 8.11a into which is inserted planoconvex lens 8.2a, posterior lens ring 8.2p and posterior lens groove 8.11p into which is inserted posterior membrane lens holder 8.2ph holding membrane lens 8.2m and membrane lens ring 8.2*mr*; bellows 8.2*b*; refractive hydraulic fluid chamber defined by anterior lens 8.2*a*, bellows 8.2*b*, membrane lens 8.2*m* and its holder 8.2*ph*, and containing refractive hydraulic fluid 8.2*f*. Also shown are fill-purge ports 8.2*fp*.

Figure 8:
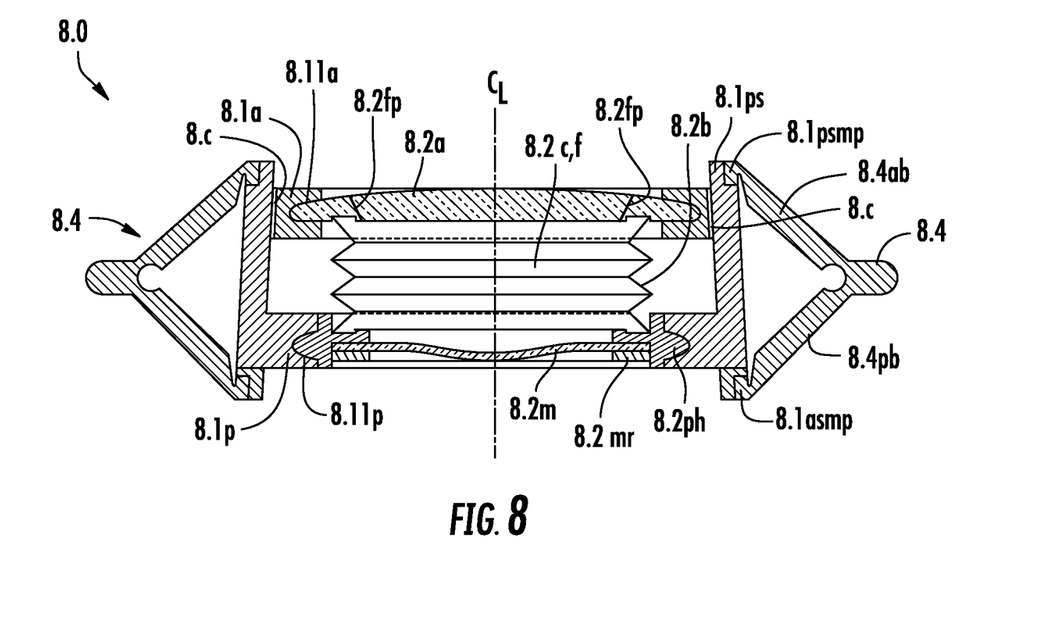
FIG. 8 is a version of FIG. 6 for actuation of a hydraulic lens, and in accordance with the present invention.
Figure 8A:
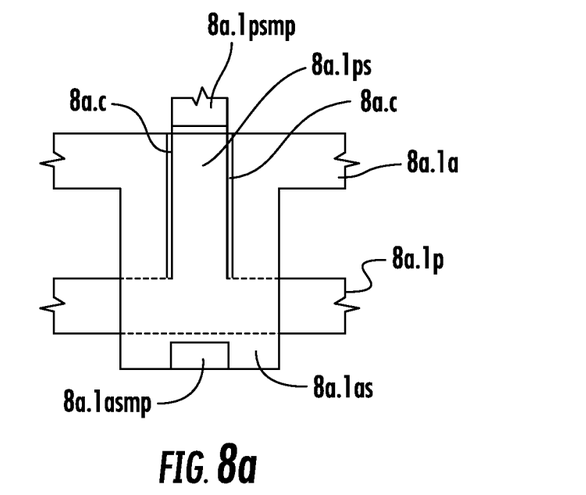
FIG. 8a is a detail view of the mounting pads and struts of FIG. 8, and in accordance with the present invention.

Hydraulic lenses of the kind shown in FIGS. 4 and 8 are, however, made accommodative by moving rings 4.1*a*, 4.1*p* and 8.1*a*, 8.1*p* closer together, just the opposite of the two fixed focus lens AIOLs of FIGS. 1, 3, and 6, and to effect this posterior ring 8.1*p* further comprises strut 8.1*ps* (8*a*.1*ps* in FIG. 8*a*) and anterior ring 8.1*p* further comprises strut 8.1*as* (hidden by the sectioning for FIG. 8, but shown as 8*a*.1*as* in FIG. 8*a*).

Thus, when anterior bifurcated haptic branches 8.4*ab* are fixedly affixed to mounting pads 8.1*psmp* and posterior bifurcated haptic branches are fixedly affixed to mounting pads 8.1*asmp* (8*a*.1*psmp* and 8*a*.1*asmp* respectively in FIG. 8*a*), and haptics 8.4 are brought closer together by the accommodative contraction of the capsule (not shown in FIG. 8) rings 8.1*a* and 8.1*p* will be brought closer together, making the hydraulic lens of FIG. 8 and its embodiments more accommodative.

The FIG. 8 configuration, however, involves sliding motion between components in close proximity, and while this is partially addressed by the clearances 8.*c* between struts 8.1*ps* and anterior rings 8.1*a* as shown in FIG. 8 and between struts 8*a*.1*ps* and 8*a*.1*as* as shown in FIG. 8*a*, these small spaces are ideal hiding places for bacteria and/or cells left over from crystalline lens extraction, and these cells can multiply, clog these spaces and inhibit the accommodative translation of rings 8.1*a*, 8.1*p* of FIG. 8. While coating and/or impregnation with cell growth inhibitors such as fu5 can address this problem, such coating or impregnating substances may not be well tolerated by the eye. Sharp edges have, however proven effective in preventing cell migration onto conventional IOLs, and can also be effective for the purpose here.

While FIG. 6 and its embodiments are viable alternatives to those of FIGS. 1 and 3, those of FIG. 8 are less so with respect to FIG. 4 because of the above.

Thus the new, novel and useful features of the aligner-actuators of the present invention have been disclosed and described, as have two-fixed-focus-lens AIOLs and hydraulic lens AIOLs actuated thereby. The AIOLs of this invention are intended for implantation in the capsules of eyes from which crystalline lenses, cataractous or otherwise, have been extracted, and are shown as such in FIG. 3 herein, this despite the age-related decrease in the accommodative change in capsule diameters (see M. A. Croft, et al, "Extralenticular and Lenticular Aspects of Accommodation and Presbyopia in Human and Monkey Eyes", IOVS Manuscript, IOVS 12-10846, Jun. 6, 2013) and the retention of accommodative change in ciliary body muscle diameter despite age (see Strenk et al, "Magnetic resonance imaging of aging, accommodating phakic and pseudophakic ciliary muscle diameters" J. Catarac Ref rac surg. 2006 November 32 (11) 1792-1798 doi:10.1016/j.jcrs.2006.05.031) because arrangements involving direct contact with the ciliary body muscle are not well tolerated by the eye, as mentioned earlier herein.

Materials suitable for use in the manufacture of the fixed-focus lenses of the AIOLs of FIGS. 1-4 and 6, 8 and 9 are typically the acrylic or the silicone polymers familiar from commercially available IOLs. Materials suitable for the rings, struts, pivots and haptics of the bifurcated haptic aligner-actuators illustrated and described herein are the haptic and strut materials familiar both from the prior art cited herein, and from commercially available AIOLs such as Crystalens™ and SynchronyVu™.

Definitions

The term "biocompatible" as used herein refers to assemblies, subassemblies, components and materials of the present invention that neither react adversely with one another when implanted in an eye, nor adversely affect the eye and/or its components when implanted therein. Such materials include the acrylic and silicone polymer lens materials and the haptic materials familiar from commercially available IOLs and AIOLs.

The terms "net negative" and "net positive" as used herein refer to negative posterior and positive anterior lenses respectively that are appropriate for two lens AIOLs. Such lenses may also include correction for aberrations of the eye for which they are intended and/or the lenses themselves.

The terms "pivot", "pivotably connected" and "pivotably coupled" as used herein refer not only to the classical definitions thereof, but also the bending grooves described and illustrated herein.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A bifurcated haptic aligner-actuator (BHAA) actuated accommodative intraocular lens (AIOL) for implantation in a capsule of an eye from which a crystalline lens has been extracted, the AIOL comprising the BHAA and at least one lens:
   the BHAA comprising an anterior lens ring and a posterior lens ring,
   each lens ring further comprising one of a lens retention groove, a lens retention ridge and a component of a hydraulic lens assembly;
   the BHAA further comprising a plurality of greater than two spaced apart center-pivoted struts a subplurality "n" of the plurality of struts being spaced 360/n degrees apart, each of the plurality of struts comprising an anterior part, a posterior part, a first pivot pivotably coupling a posterior end of the anterior part of a strut to an anterior end of the posterior part of the same strut, a second pivot pivotably coupling an anterior end of the anterior part of the strut to the anterior ring, and a third pivot pivotably coupling a posterior end of the posterior part of the strut to the posterior ring;
   the BHAA further comprising a first plurality of "n" bifurcated haptics, each bifurcated haptic further comprising an anterior branch, a posterior branch and an outboard end, and wherein each anterior branch of each haptic is pivotably coupled to an anterior part of each one of the subplurality "n" of said struts a first distance from the first pivot and each posterior branch of each haptic is pivotally coupled to a posterior part of the same strut a second distance from the first pivot, wherein each anterior branch and posterior branch of each bifurcated haptic further comprises a biasing portion that biases the AIOL one of accommodatively and disaccommodatively, and wherein the outboard end of each bifurcated haptic comprises an outboard end configured for retention and actuation with respect to accommodation and disaccommodation by the capsule; the AIOL further comprising one of a fixed focus lens retained by the anterior ring, a pair of fixed focus lenses one of which is retained by the anterior ring and the other by the posterior ring, and a hydraulic lens having a fixed focus lens part and a membrane lens assembly, wherein the fixed focus lens part is integral with or retained by one of the anterior and posterior rings, and the membrane lens assembly part is integral with or retained by the other of the anterior and posterior rings.

2. The BHAA of claim 1, wherein the subplurality "n" equals two struts, and wherein a first strut of the two struts of the subplurality "n", and its respective first associated haptic, is spaced 180 degrees apart from a second strut of the two struts of the subplurality "n", and its respective second associated haptic.

3. The BHAA of claim 1, wherein at least all of the same ordinal-numbered pivotal couplings of the struts are one of biased bending grooves and hinges.

4. The BBHA of claim 3, wherein at least all of the same ordinal-numbered pivotal couplings of the struts are biased bending grooves that bias the AIOL the same one of accommodatively and disaccommodatively.

5. The BHAA of claim 1, wherein at least one edge of each ring proximal to a lens further comprises an edge sharp enough to discourage migration of cells left over from capsulorhexis and/or lens extraction to a lens of the AIOL.

6. The BHAA AIOL of claim 1 wherein the AIOL is a two fixed focus lens AIOL and the two fixed focus lenses comprise a net positive anterior lens retained by the anterior ring and a net negative posterior lens retained by the posterior ring;

wherein the AIOL is disaccommodatively biased by at least one of the strut bending grooves, the biasing portions of the haptics and a spacer-actuator; and wherein the AIOL is made accommodative by at least one of centripetal forces applied to the outboard ends of the haptics by the capsule and centripetal forces applied to the outboard ends of the haptics by the capsule and a tensioning ring affixed to the capsule.

7. The BHAA AIOL of claim 1, wherein the AIOL is a one fixed focus lens AIOL and the one fixed focus lens comprises a net positive anterior lens retained by the anterior ring; the AIOL further comprising disaccommodatively biasing by at least one of the strut bending grooves, the biasing portions of the haptics and a spacer-actuator, and wherein the AIOL is made accommodative by at least one of centripetal forces applied to the outboard ends of the haptics by the capsule and centripetal forces applied to the outboard ends of the haptics by the capsule and a tensioning ring affixed to the capsule.

8. The BHA A AIOL of claim 1, wherein the AIOL is a hydraulic AIOL and the hydraulic lens comprises one of a fixed focus lens part of the hydraulic lens one of retained by and integral with one of the anterior and the posterior rings, and a membrane lens assembly part of the hydraulic lens one of retained by and integral with the other of the anterior and posterior rings, the AIOL further comprising disaccommodative biasing by at least one of the strut bending grooves, the biasing portions of the haptics and a spacer-actuator, and wherein the hydraulic AIOL is made accommodative by at least one of centripetal forces applied to the outboard ends of the haptics by the capsule and centripetal forces applied to the outboard ends of the haptics by the capsule and centripetral forces applied to the capsule by a tensioning ring.

9. A bifurcated haptic aligner-actuator (BHAA) actuated accommodative intraocular lens (AIOL) for implantation in a capsule of an eye from which a crystalline lens has been extracted, the AIOL comprising the BHAA and at least one lens:

the BHAA comprising an anterior lens ring and a posterior lens ring, each lens ring further comprising one of a lens retention groove, a lens retention ridge and a component of a hydraulic lens assembly;

the BHAA further comprising a plurality of greater than two spaced apart center-pivoted struts a subplurality "n" of the plurality of struts being spaced 360/n degrees apart, each of the plurality of struts comprising an anterior part, a posterior part, a first pivot pivotably coupling a posterior end of the anterior part of a strut to an anterior end of the posterior part of the same strut, a second pivot pivotably coupling an anterior end of the anterior part of the strut to the anterior ring, and a third pivot pivotably coupling a posterior end of the posterior part of the strut to the posterior ring; and a first plurality of "n" bifurcated haptics, each bifurcated haptic comprising an anterior branch, a posterior branch and an outboard end, wherein each anterior branch of each haptic is pivotably coupled to an anterior ring a same distance from an anterior face of an anterior ring and each posterior branch of each haptic is pivotably coupled to a posterior ring the same distance from a posterior face of the posterior ring, wherein each anterior branch and posterior branch of each bifurcated haptic further comprises a biasing portion that biases the AIOL one of accommodatively and disaccommodatively, wherein the outboard end of each bifurcated haptic further comprises an outboard end configured for retention and actuation with respect to accommodation and disaccommodation by the capsule;

the AIOL further comprising one of a fixed focus lens retained by the anterior ring, a pair of fixed focus lenses one of which is retained by the anterior ring and the other by the posterior ring and a hydraulic lens having a fixed focus lens part and a membrane lens assembly, wherein the fixed focus lens part is integral with or retained by one of the anterior and posterior rings and the membrane lens assembly part is integral with or retained by the other of the anterior and posterior rings.

10. The BHA A AIOL of claim 1, wherein the AIOL is a hydraulic AIOL and the hydraulic lens comprises one of a fixed focus lens part of the hydraulic lens one of retained by and integral with one of the anterior and the posterior rings, and a membrane lens assembly part of the hydraulic lens one of retained by and integral with the other of the anterior and posterior rings, the AIOL further comprising disaccommodative biasing by at least one of the strut bending grooves, the biasing portions of the haptics and a spacer-actuator, and wherein the hydraulic AIOL is made accommodative by at least one of centripetal forces applied to the outboard ends of the haptics by the capsule and centripetal forces applied to the outboard ends of the haptics by the capsule and centripetral forces applied to the capsule by a tensioning ring.

\* \* \* \* \*